(12) United States Patent
Stegmann et al.

(10) Patent No.: US 6,642,026 B2
(45) Date of Patent: *Nov. 4, 2003

(54) METHOD OF PRODUCING BIOLOGICALLY ACTIVE HUMAN ACIDIC FIBROBLAST GROWTH FACTOR AND ITS USE IN PROMOTING ANGIOGENESIS

(75) Inventors: Thomas J. Stegmann, Petersberg (DE); Vitaliy A. Kordyum, Kiev (UA); Iryna Yu. Slavchenko, Kiev (UA); Svitlana I. Chernykh, Kiev (UA); Oleksandr F. Vozianov, Kiev (UA)

(73) Assignee: Phage Biotechnology Corporation, Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,945

(22) Filed: Aug. 15, 2001

(65) Prior Publication Data
US 2002/0155532 A1 Oct. 24, 2002

Related U.S. Application Data
(60) Provisional application No. 60/225,406, filed on Aug. 15, 2000.

(51) Int. Cl.$^7$ .......................... C12P 15/09; C12P 15/18; C12P 21/02; C12P 39/00; C12N 7/01
(52) U.S. Cl. .................... 435/69.1; 435/69.4; 435/69.5; 435/71.2; 435/3; 435/5; 435/6; 435/7.37; 435/235.1; 435/325
(58) Field of Search .................. 435/3, 5, 6, 7.37, 435/69.1, 235.1, 325, 69.5, 69.4, 71.2

(56) References Cited

U.S. PATENT DOCUMENTS 5,571,790 A  11/1996  Jaye et al.
6,268,178 B1  7/2001  Kordyum et al.

FOREIGN PATENT DOCUMENTS

EP   0 298 723 A1   1/1989
WO   WO 98/39436   9/1998

OTHER PUBLICATIONS

Blaber et al. Biophysical Journal 1999, vol. 77, pp. 470–477.*
International Search Report from International Application No.: PCT/US01/25537, dated Sep. 19, 2002.

* cited by examiner

Primary Examiner—James Housel
Assistant Examiner—Bao Qun Li
(74) Attorney, Agent, or Firm—Knobbe, Martens, Olson & Bear, LLP

(57) ABSTRACT

The gene of human acidic fibroblast growth factor 155 (haFGF 155) has been obtained by chemical synthesis. The nucleotide sequence of haFGF 155 gene has been deduced on the basis of haFGF 155 amino acid sequence as described in the literature. The amino acid sequence of the synthesized haFGF 155 does not differ from those described in the literature. The nucleotide sequence of haFGF gene differs from those described previously. For chemical synthesis of haFGF 155 gene, codons were used which are the ones most often used by *E. coli* in highly expressed *E. coli* proteins. A plasmid with haPGF 155 (phaFGF 155) gene was obtained and was used to transform *E. coli*. Production of haFGF 154 protein was achieved by cultivation of the producer strain under conditions which slow down the lytic development of lambda phage. The haFGF 154 protein accumulated in culture medium in a soluble condition as a result of the producer strain cells lysis by the lambda phage. The haFGF 154 protein constituted 20% of the soluble protein accumulated in the culture medium and its biological activity was demonstrated by its ability to generate new vessels (angiogenesis). The initiator methionine residue at position 1 of the FGF 155 protein was completely removed during protein synthesis resulting in an FGF 154 amino acid product. The use of the phage-dependent method to produce other forms of the haFGF protein is also disclosed.

18 Claims, 12 Drawing Sheets

```
                BsaBI
                -----
        BglII           VspI            BfmI            MbiI            XbaI
        ~~~~~           ~~~~            ~~~~            ~~~~            ~~~~
4951  GCGTAGAGGATCGAGATCTCGATCCCGCGAAATTAATACGACTCA CTATAGGGGAATTGTGAGCGGATAACAATTCCCCTCTAGAAATAA
      CGCATCTCCTAGCTCTAGAGCTAGGGCGCTTTAATTATGCTGAGT GATATCCCCTTAACACTCGCCTATTGTTAAGGGGAGATCTTTATT

+2                              MetAlaGluGlyGlu IleThrThrPheThrAlaLeuThrGluLysPheAsnLeuProPr
                                                                                         HpaI
                                                                                         ----
                                                                   HindII           SmaI
                                                                   ------           ~~
                      NdeI   Eco57I                                HincII           AvaI
                      ----   ------                                ~~~~~~           ~~
5041  TTTTGTTTAACTTTAAGAAGGAGATATACATATGGCTGAAGGGGA AATCACCACCTTTACAGCGTTAACGGAGAAATTTAACCTTCCGCC
      AAAACAAATTGAAATTCTTCCTCTATATGTATACCGACTTCCCCT TTAGTGGTGGAAATGTCGCAATTGCCTCTTTAAATTGGAAGGCGG +2 oGlyAsnTyrLysLysProLysLeuLeuTyrCysSerAsnGlyGly HisPheLeuArgIleLeuProAspGlyThrValAspGlyThrAr
     SmaI                                    PstI
     ~~~~                                    ~~~~~~
     AvaI           HindIII      BfmI                       EcoRI                       NruI
     ~~~            ~~~~~~~      ~~~~                       ~~~~~                       ~~~
5131  CGGGAATTACAAAAAACCCAAGCTTCTTTACTGCAGTAACGGAGG ACACTTCCTGCGAATTCTGCCAGATGGCACAGTAGATGGGACTCG
      GCCCTTAATGTTTTTTGGGTTCGAAGAAATGACGTCATTGCCTCC TGTGAAGGACGCTTAAGACGGTCTACCGTGTCATCTACCCTGAGC +2 gAspArgSerAspGlnHisIleGlnLeuGlnLeuSerAlaGluSer ValGlyGluValTyrIleLysSerThrGluThrGlyGlnTyrLe
                                                                                SalI
                                                                                ~~~~
                                                                   HindII           RsaI
     PvuI                                                          ------           ~~~~
     ~~~~
                       NruI           PvuII      XmaIII            HincII           MlsI Csp6I
                       ~~~            ~~~~~      ~~~~~~            ~~~~~~           ~~~~~~~~~~~
5221  CGATCGCTCCGACCAGCACATTCAGCTGCAACTCTCGGCCGAAAG CGTTGGAGAGGTCTATATCAAGTCGACGGAGACTGGCCAGTACCT
      GCTAGCGAGGCTGGTCGTGTAAGTCGACGTTGAGAGCCGGCTTTC GCAACCTCTCCAGATATAGTTCAGCTGCCTCTGACCGGTCATGGA +2 uAlaMetAspThrAspGlyLeuLeuTyrGlySerGlnThrProAsn GluGluCysLeuPheLeuGluArgLeuGluGluAsnHisTyrAs
     StyI
     ~~~~~
     NcoI                                    Mval269I   XbaI
     ~~~~                                    ~~~~~~~~   ~~~~
5311  TGCCATGGACACCGATGGGCTTCTGTATGGCTCACAGACGCCTAA CGAAGAATGCTTGTTTCTAGAAAGACTAGAAGAAAACCATTACAA
      ACGGTACCTGTGGCTACCCGAAGACATACCGAGTGTCTGCGGATT GCTTCTTACGAACAAAGATCTTTCTGATCTTCTTTTGGTAATGTT +2 nThrTyrIleSerLysLysHisAlaGluLysAsnTrpPheValGly LeuLysLysAsnGlySerCysLysArgGlyProArgThrHisTy
     RsaI
     ~~~~
     Csp6I                              StuI
     ~~~~~                              ~~~~
5401  CACGTACATATCGAAAAAACATGCAGAGAAGAACTGGTTTGTAGG CCTTAAAAAAAATGGTTCCTGTAAGCGTGGACCACGGACTCACTA
      GTGCATGTATAGCTTTTTTGTACGTCTCTTCTTGACCAAACATCC GGAATTTTTTTTACCAAGGACATTCGCACCTGGTGCCTGAGTGAT +2 rGlyGlnLysAlaIleLeuPheLeuProLeuProValSerSerAsp ***
                                                                         SalI        XmaIII
                                                                         ~~~~        ~~~~~~
                                              SacI              EcoRI SacI  HindII       XhoI
                                              ~~~~              ~~~~~ ~~~~  ~~~~~~       ~~~~
     MlsI                                   Ecl136II         BamHI     Ecl136IIHincIIHindIII NotIAvaI
     ~~~~~                                  ~~~~~~~~         ~~~~~     ~~~~~~~~~~~~~~~~~~~~ ~~~~~~~~
5491  TGGCCAAAAGGCTATCTTGTTCCTGCCACTACCAGTGAGCTCCGA CTAAGGATCCGAATTCGAGCTCCGTCGACAAGCTTGCGGCCGCAC
      ACCGGTTTTCCGATAGAACAAGGACGGTGATGGTCACTCGAGGCT GATTCCTAGGCTTAAGCTCGAGGCAGCTGTTCGAACGCCGGCGTG
```

**CHEMICALLY SYNTHESIZED haFGF GENE AND
CORRESPONDING AMINO ACID SEQUENCE**

*FIG. 1*

| | | | | | | | | |
|---|---|---|---|---|---|---|---|---|
| FGF fr HUMECGFB | TTC | GCC | CTG | ACC | AAG | AAT | CTG | CCT | CCA |
| haFGF 155 | TTT | GCG | TTA | ACG | AAA | AAC | CTT | CCG | CCC |
| № amino acid | 009 | 011 | 012 | 013 | 015 | 017 | 018 | 019 | 020 |
| | Phe | Ala | Leu | Thr | Lys | Asn | Leu | Pro | Pro |

| | | | | | | | | |
|---|---|---|---|---|---|---|---|---|
| FGF fr HUMECGFB | AAG | AAG | AAA | CTC | CTC | TGT | AGC | GGG | GGC |
| haFGF 155 | AAA | AAA | AAG | CTT | CTT | TGC | AGT | GGA | GGA |
| № amino acid | 024 | 025 | 027 | 028 | 029 | 031 | 032 | 034 | 035 |
| | Lys | Lys | Lys | Leu | Leu | Cys | Ser | Gly | Gly |

| | | | | | | | | |
|---|---|---|---|---|---|---|---|---|
| FGF fr HUMECGFB | AGG | ATC | CTT | CCG | GTG | ACA | AGG | GAC | AGG |
| haFGF 155 | CGA | ATT | CTG | CCA | GTA | ACT | CGC | GAT | CGC |
| № amino acid | 039 | 040 | 041 | 042 | 046 | 049 | 050 | 051 | 052 |
| | Arg | Ile | Leu | Pro | Val | Thr | Arg | Asp | Arg |

| | | | | | | | | |
|---|---|---|---|---|---|---|---|---|
| FGF fr HUMECGFB | AGC | CAG | AGT | GCG | GTG | GGG | GTG | ATA | AGT |
| haFGF 155 | TCC | CAA | TCG | GCC | GTT | GGA | GTC | ATC | TCG |
| № amino acid | 053 | 060 | 062 | 063 | 066 | 067 | 069 | 071 | 073 |
| | Ser | Gln | Ser | Ala | Val | Gly | Val | Ile | Ser |

| | | | | | | | | |
|---|---|---|---|---|---|---|---|---|
| FGF fr HUMECGFB | ACC | TTG | GAC | TTA | TAC | ACA | CCA | AAT | GAG |
| haFGF 155 | ACG | CTT | GAT | CTG | TAT | ACG | CCT | AAC | GAA |
| № amino acid | 074 | 080 | 085 | 088 | 089 | 093 | 094 | 095 | 096 |
| | Thr | Leu | Asp | Leu | Tyr | Thr | Pro | Asn | Glu |

| | | | | | | | | |
|---|---|---|---|---|---|---|---|---|
| FGF fr HUMECGFB | TGT | TTC | CTG | AGG | CTG | GAG | GAG | ACC | TAT |
| haFGF 155 | TGC | TTT | CTA | AGA | CTA | GAA | GAA | ACG | TAC |
| № amino acid | 098 | 100 | 101 | 103 | 104 | 105 | 106 | 111 | 112 |
| | Cys | Phe | Leu | Arg | Leu | Glu | Glu | Thr | Tyr |

| | | | | | | | | |
|---|---|---|---|---|---|---|---|---|
| FGF fr HUMECGFB | TCC | AAG | AAG | AAT | GTT | CTC | AAG | AAG | GGG |
| haFGF 155 | TCG | AAA | AAA | AAC | GTA | CTT | AAA | AAA | GGT |
| № amino acid | 114 | 115 | 116 | 121 | 124 | 126 | 127 | 128 | 130 |
| | Ser | Lys | Lys | Asn | Val | Leu | Lys | Lys | Gly |

| | | | | | | | | |
|---|---|---|---|---|---|---|---|---|
| FGF fr HUMECGFB | AGC | TGC | AAA | CGC | GGT | CCT | CAG | AAA | GCA |
| haFGF 155 | TCC | TGT | AAG | CGT | GGA | CCA | CAA | AAG | GCT |
| № amino acid | 131 | 132 | 133 | 134 | 135 | 136 | 142 | 143 | 144 |
| | Ser | Cys | Lys | Arg | Gly | Pro | Gln | Lys | Ala |

| | | | | | | | | |
|---|---|---|---|---|---|---|---|---|
| FGF fr HUMECGFB | TTT | CTC | CCC | CTG | GTC | TCT | TCT | GAT | |
| haFGF 155 | TTC | CTG | CCA | CTC | GTG | AGC | TCC | GAC | |
| № amino acid | 147 | 148 | 149 | 150 | 152 | 153 | 154 | 155 | |
| | Phe | Leu | Pro | Leu | Val | Ser | Ser | Asp | |

MODIFICATION IN MOLECULE haFGF 155 CODONS.
FGF fr HUMECGFB—THE SEQUENCE FROM GENBANK(at NCBI), haFGF 155
-THE SEQUENCE SYNTHESIZED BY THE INVENTION AUTHORS.

*FIG.2*

FGF-1(154aa) PURIFICATON

LANE 1: CRUDE MEDIA; YIELD: 225 mg FGF-1/LITER
2: HEPARIN-SEPHAROSE COLUMN
3: HPLC: C-18 COLUMN

OVERALL PURIFICATION YIELD: 65%
BIOACTIVITY: EQUIPOTENT WITH FGF-1 (SIGMA CHEM) IN:
1) 3T3 CELL PROLIFERATION ASSAY, AND
2) RAT HIND LIMB ANGIOGENESIS ASSAY

```
                    BsaBI
                  ~~~~~~~~~
              BsaBI
            ~~~~~~~~~~
         BglII          VspI            BfmI          MbiI              XbaI
        ~~~~~~         ~~~~~~          ~~~~~~       ~~~~~~             ~~~~~~
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT

+2                                 MetAsnTyrLysLys ProLysLeuLeuTyrCysSerAsnGlyGlyHisPheLeuArgIl
                                                                              PstI
                                                                            ~~~~~~
                        NdeI                      HindIII     BfmI                          EcoRI
                      ~~~~~~                      ~~~~~~~    ~~~~~~                          ~~~~
5041 TTTTGTTTAACTTTAAGAAGGAGATATACATATGAATTACAAAAA ACCCAAGCTTCTTTACTGCAGTAACGGAGGACACTTCCTGCGAAT
     AAAACAAATTGAAATTCTTCCTCTATATGTATACTTAATGTTTTT TGGGTTCGAAGAAATGACGTCATTGCCTCCTGTGAAGGACGCTTA +2 eLeuProAspGlyThrValAspGlyThrArgAspArgSerAspGln HisIleGlnLeuGlnLeuSerAlaGluSerValGlyGluValTy
                                            PvuI
                                          ~~~~~~
      EcoRI                 NruI                        PvuII      XmaIII
     ~~~~~~               ~~~~~~                       ~~~~~~     ~~~~~~
5131 TCTGCCAGATGGCACAGTAGATGGGACTCGCGATCGCTCCGACCA GCACATTCAGCTGCAACTCTCGGCCGAAAGCGTTGGAGAGGTCTA
     AGACGGTCTACCGTGTCATCTACCCTGAGCGCTAGCGAGGCTGGT CGTGTAAGTCGACGTTGAGAGCCGGCTTTCGCAACCTCTCCAGAT +2 rIleLysSerThrGluThrGlyGlnTyrLeuAlaMetAspThrAsp GlyLeuLeuTyrGlySerGlnThrProAsnGluGluCysLeuPh
           SalI
         ~~~~~~
           HindII         RsaI         StyI
         ~~~~~~          ~~~~          ~~~~
           HincII       MlsI Csp6I    NcoI                                      Mva1269I
         ~~~~~~        ~~~~~~~~~~    ~~~~~~                                    ~~~~~~
5221 TATCAAGTCGACGGAGACTGGCCAGTACCTTGCCATGGACACCGA TGGGCTTCTGTATGGCTCACAGACGCCTAACGAAGAATGCTTGTT
     ATAGTTCAGCTGCCTCTGACCGGTCATGGAACGGTACCTGTGGCT ACCCGAAGACATACCGAGTGTCTGCGGATTGCTTCTTACGAACAA +2 eLeuGluArgLeuGluGluAsnHisTyrAsnThrTyrIleSerLys LysHisAlaGluLysAsnTrpPheValGlyLeuLysLysAsnGl
                                            RsaI
                                           ~~~~
      XbaI                Csp6I                                              StuI
     ~~~~~~              ~~~~~~                                             ~~~~~~
5311 TCTAGAAAGACTAGAAGAAAACCATTACAACACGTACATATCGAA AAAACATGCAGAGAAGAACTGGTTTGTAGGCCTTAAAAAAAATGG
     AGATCTTTCTGATCTTCTTTTGGTAATGTTGTGCATGTATAGCTT TTTTGTACGTCTCTTCTTGACCAAACATCCGGAATTTTTTTTACC +2 ySerCysLysArgGlyProArgThrHisTyrGlyGlnLysAlaIle LeuPheLeuProLeuProValSerSerAsp***
                                                                            SacI
                                                                          ~~~~~~
                 MlsI                             Ecl136II         BamHIEcoRI
               ~~~~~~                            ~~~~~~           ~~~~~~~~~~~~
5401 TTCCTGTAAGCGTGGACCACGGACTCACTATGGCCAAAAGGCTAT CTTGTTCCTGCCACTACCAGTGAGCTCCGACTAAGGATCCGAATT
     AAGGACATTCGCACCTGGTGCCTGAGTGATACCGGTTTTCCGATA GAACAAGGACGGTGATGGTCACTCGAGGCTGATTCCTAGGCTTAA SacI   SalI
        ~~~~   ~~~~
         EcoRI   HindII       XmaIII    XhoI
        ~       ~~~~~~       ~~~~~~    ~~~~~~
        Ecl136IIHincIIHindIII NotI      AvaI
       ~~~~~~~~~~~~~~~~~~~~ ~~~~      ~~~~
5491 CGAGCTCCGTCGACAAGCTTGCGGCCGCACTCGAGCACCACCAC ACCACCACTGAGATCCGGCTGCTAACAAAGCCCGAAAGGAAGCTG
     GCTCGAGGCAGCTGTTCGAACGCCGGCGTGAGCTCGTGGTGGTG TGGTGGTGACTCTAGGCCGACGATTGTTTCGGGCTTTCCTTCGAC
```

NUCLEOTIDE AND AMINO ACID SEQUENCE FOR CHEMICALLY SYNTHESIZED HUMAN A FGF (134 AMINO ACIDS)

FIG. 6

```
              BsaBI
           ~~~~~~~~~~~

BsaBI
      ~~~~~~~~~~~~

BglII           VspI            BfmI          MbiI              XbaI
      ~~~~~           ~~~~~           ~~~~~         ~~~~~             ~~~~~
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT
```

```
                              MetPheAsnLeuPro ProGlyAsnTyrLysLysProLysLeuLeuTyrCysSerAsnGl
  +2                                          SmaI                              PstI
                                             ~~~~~                              ~~~~~

NdeI              AvaI               HindIII    BfmI
                         ~~~~~             ~~~~~              ~~~~~~~    ~~~~~
5041 TTTTGTTTAACTTTAAGAAGGAGATATACATATGTTTAACCTTCC GCCCGGGAATTACAAAAAACCCAAGCTTCTTTACTGCAGTAACGG
     AAAACAAATTGAAATTCTTCCTCTATATGTATACAAATTGGAAGG CGGGCCCTTAATGTTTTTTGGGTTCGAAGAAATGACGTCATTGCC
```

```
  +2 yGlyHisPheLeuArgIleLeuProAspGlyThrValAspGlyThr ArgAspArgSerAspGlnHisIleGlnLeuGlnLeuSerAlaGl
                                                     PvuI
                                                    ~~~~~~
            EcoRI                         NruI                       PvuII           XmaIII
            ~~~~~                        ~~~~~                       ~~~~~           ~~~~~~
5131 AGGACACTTCCTGCGAATTCTGCCAGATGGCACAGTAGATGGGAC TCGCGATCGCTCCGACCAGCACATTCAGCTGCAACTCTCGGCCGA
     TCCTGTGAAGGACGCTTAAGACGGTCTACCGTGTCATCTACCCTG AGCGCTAGCGAGGCTGGTCGTGTAAGTCGACGTTGAGAGCCGGCT
```

```
  +2 uSerValGlyGluValTyrIleLysSerThrGluThrGlyGlnTyr LeuAlaMetAspThrAspGlyLeuLeuTyrGlySerGlnThrPr
                         SalI
                        ~~~~~~
                 HindII             RsaI         StyI
                 ~~~~~~             ~~~~~        ~~~~~~
                 HincII     MlsI Csp6I    NcoI
                 ~~~~~~     ~~~~~~~~~~    ~~~~~
5221 AAGCGTTGGAGAGGTCTATATCAAGTCGACGGAGACTGGCCAGTA CCTTGCCATGGACACCGATGGGCTTCTGTATGGCTCACAGACGCC
     TTCGCAACCTCTCCAGATATAGTTCAGCTGCCTCTGACCGGTCAT GGAACGGTACCTGTGGCTACCCGAAGACATACCGAGTGTCTGCGG
```

```
  +2 oAsnGluGluCysLeuPheLeuGluArgLeuGluGluAsnHisTyr AsnThrTyrIleSerLysLysHisAlaGluLysAsnTrpPheVa
                                                     RsaI
                                                    ~~~~~
         Mval2691     XbaI                          Csp6I
         ~~~~~~~      ~~~~~                         ~~~~~~
5311 TAACGAAGAATGCTTGTTTCTAGAAAGACTAGAAGAAAACCATTA CAACACGTACATATCGAAAAAACATGCAGAGAAGAACTGGTTTGT
     ATTGCTTCTTACGAACAAAGATCTTTCTGATCTTCTTTTGGTAAT GTTGTGCATGTATAGCTTTTTTGTACGTCTCTTCTTGACCAAACA
```

```
  +2 lGlyLeuLysLysAsnGlySerCysLysArgGlyProArgThrHis TyrGlyGlnLysAlaIleLeuPheLeuProLeuProValSerSe
                                                                                            SacI
                                                                                           ~~~~~~
         StuI                                     MlsI                            Ec1136II
         ~~~~~                                    ~~~~~                           ~~~~~~~~
5401 AGGCCTTAAAAAAAATGGTTCCTGTAAGCGTGGACCACGGACTCA CTATGGCCAAAAGGCTATCTTGTTCCTGCCACTACCAGTGAGCTC
     TCCGGAATTTTTTTTACCAAGGACATTCGCACCTGGTGCCTGAGT GATACCGGTTTTCCGATAGAACAAGGACGGTGATGGTCACTCGAG
```

```
  +2 rAsp***
                          SalI
                         ~~~~~
          EcoRI SacI HindII    XmaIII       XhoI
          ~~~~~ ~~~~ ~~~~~~    ~~~~~~       ~~~~
      BamHI    Ec1136IIHincIIHindIII NotI   AvaI
      ~~~~~    ~~~~~~~~~~~~~~~~~~~~~~~~~    ~~~~~
5491 CGACTAAGGATCCGAATTCGAGCTCCGTCGACAAGCTTGCGGCCG CACTCGAGCACCACCACCACCACCACTGAGATCGGCTGCTAACA
     GCTGATTCCTAGGCTTAAGCTCGAGGCAGCTGTTCGAACGCCGGC GTGAGCTCGTGGTGGTGGTGGTGGTGACTCTAGCCGACGATTGT
```

NUCLEOTIDE AND AMINO ACID SEQUENCE FOR CHEMICALLY SYNTHESIZED HUMAN A FGF (140 AMINO ACIDS)

ELECTROPHOREGRAMM

1-MOLECULAR WEIGHT KIT(94 000, 67 000, 43 000, 30 000 20 100, 14 400)

THE CULTURAL MEDIUM, CONTAINING:
2-haFGF 134(40 μl OF THE CULTURAL MEDIUM)
3-haFGF 140(40 μl OF THE CULTURAL MEDIUM)
4-IFNα 2B(40 μl OF THE CULTURAL MEDIUM)
5-haFGF 155(40 μl OF THE CULTURAL MEDIUM)
6-HGH(40 μl OF THE CULTURAL MEDIUM)
7-MAP(40 μl OF THE CULTURAL MEDIUM)
8-β-GALACTOSIDASE OF E. COLI(40 μl OF THE CULTURAL MEDIUM)

ELECTROPHOREGRAMM OF THE PURIFIED PRODUCTS:

1-MOLECULAR WEIGHT KIT (94 000, 67 000, 43 000, 30 000, 20 100, 14 400)
2-haFGF 134
3-haFGF 140
4-haFGF 146
5-IFN α2b
6-haFGF 155
7-MAP
8-MOLECULAR WEIGHT KIT 1 ugm recombinant haFGF 155

CONTROL

SEQUENCE LISTING

```
<160> NUMBER OF SEQ ID NOS: 8

<210> SEQ ID NO 1
<211> LENGTH: 630
<212> TYPE: DNA
<213> ORGANISM: Artificial Sequence
<220> FEATURE:
<223> OTHER INFORMATION: Chemically synthesized sequence for human
      acidic Fibroblast Growth Factor (155 amino acids) using preferred
      codons for E. coli
<221> NAME/KEY: CDS
<222> LOCATION: (122)...(590)

<400> SEQUENCE: 1
gcgtagagga tcgagatctc gatcccgcga aattaatacg actcactata ggggaattgt      60
gagcggataa caattcccct ctagaaataa ttttgtttaa ctttaagaag gagatataca     120 t atg gct gaa ggg gaa atc acc acc ttt aca gcg tta acg gag aaa ttt    169
  Met Ala Glu Gly Glu Ile Thr Thr Phe Thr Ala Leu Thr Glu Lys Phe
   1               5                  10                  15 aac ctt ccg ccc ggg aat tac aaa aaa ccc aag ctt ctt tac tgc agt      217
Asn Leu Pro Pro Gly Asn Tyr Lys Lys Pro Lys Leu Leu Tyr Cys Ser
             20                  25                  30 aac gga gga cac ttc ctg cga att ctg cca gat ggc aca gta gat ggg      265
Asn Gly Gly His Phe Leu Arg Ile Leu Pro Asp Gly Thr Val Asp Gly
         35                  40                  45 act cgc gat cgc tcc gac cag cac att cag ctg caa ctc tcg gcc gaa      313
Thr Arg Asp Arg Ser Asp Gln His Ile Gln Leu Gln Leu Ser Ala Glu
     50                  55                  60 agc gtt gga gag gtc tat atc aag tcg acg gag act ggc cag tac ctt      361
Ser Val Gly Glu Val Tyr Ile Lys Ser Thr Glu Thr Gly Gln Tyr Leu
 65                  70                  75                  80 gcc atg gac acc gat ggg ctt ctg tat ggc tca cag acg cct aac gaa      409
Ala Met Asp Thr Asp Gly Leu Leu Tyr Gly Ser Gln Thr Pro Asn Glu
                 85                  90                  95 gaa tgc ttg ttt cta gaa aga cta gaa gaa aac cat tac aac acg tac      457
```

```
Glu Cys Leu Phe Leu Glu Arg Leu Glu Asn His Tyr Asn Thr Tyr
            100                 105                 110
ata tcg aaa aaa cat gca gag aag aac tgg ttt gta ggc ctt aaa aaa    505
Ile Ser Lys Lys His Ala Glu Lys Asn Trp Phe Val Gly Leu Lys Lys
        115                 120                 125
aat ggt tcc tgt aag cgt gga cca cgg act cac tat ggc caa aag gct    553
Asn Gly Ser Cys Lys Arg Gly Pro Arg Thr His Tyr Gly Gln Lys Ala
130                 135                 140
atc ttg ttc ctg cca cta cca gtg agc tcc gac taa g gatccgaatt       600
Ile Leu Phe Leu Pro Leu Pro Val Ser Ser Asp  *
145                 150                 155 cgagctccgt cgacaagctt gcggccgcac                                   630

<210> SEQ ID NO 2
<211> LENGTH: 155
<212> TYPE: PRT
<213> ORGANISM: Homo sapiens

<400> SEQUENCE: 2

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 3
<211> LENGTH: 468
<212> TYPE: DNA
<213> ORGANISM: Homo sapiens

<400> SEQUENCE: 3
atggctgaag ggaaatcac caccttcaca gccctgaccg agaagtttaa tctgcctcca     60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac aaatgagga atgtttgttc    300 ctggaaaggc tggaggagaa ccattacaac acctatatat ccaagaagca tgcagagaag    360
aattggtttg ttggcctcaa gaagaatggg agctgcaaac gcgtcctcg gactcactat    420 ggccagaaag caatcttgtt tctccccctg ccagtctctt ctgattaa                 468
```

```
<210> SEQ ID NO 4
<211> LENGTH: 630
<212> TYPE: DNA
<213> ORGANISM: Artificial Sequence
<220> FEATURE:
<223> OTHER INFORMATION: Chemically synthesized sequence for human
      acidic Fibroblast Growth Factor (134 amino acids) using preferred
      codons for E. coli
<221> NAME/KEY: CDS
<222> LOCATION: (122)...(526)

<400> SEQUENCE: 4
gcgtagagga tcgagatctc gatcccgcga aattaatacg actcactata ggggaattgt    60
gagcggataa caattcccct ctagaaataa ttttgtttaa ctttaagaag gagatataca   120 t atg aat tac aaa aaa ccc aag ctt ctt tac tgc agt aac gga gga cac   169
  Met Asn Tyr Lys Lys Pro Lys Leu Leu Tyr Cys Ser Asn Gly Gly His
  1               5                   10                  15 ttc ctg cga att ctg cca gat ggc aca gta gat ggg act cgc gat cgc    217
Phe Leu Arg Ile Leu Pro Asp Gly Thr Val Asp Gly Thr Arg Asp Arg
            20                  25                  30 tcc gac cag cac att cag ctg caa ctc tcg gcc gaa agc gtt gga gag    265
Ser Asp Gln His Ile Gln Leu Gln Leu Ser Ala Glu Ser Val Gly Glu
        35                  40                  45 gtc tat atc aag tcg acg gag act ggc cag tac ctt gcc atg gac acc    313
Val Tyr Ile Lys Ser Thr Glu Thr Gly Gln Tyr Leu Ala Met Asp Thr
    50                  55                  60 gat ggg ctt ctg tat ggc tca cag acg cct aac gaa gaa tgc ttg ttt    361
Asp Gly Leu Leu Tyr Gly Ser Gln Thr Pro Asn Glu Glu Cys Leu Phe
65                  70                  75                  80 cta gaa aga cta gaa gaa aac cat tac aac acg tac ata tcg aaa aaa    409
Leu Glu Arg Leu Glu Glu Asn His Tyr Asn Thr Tyr Ile Ser Lys Lys
                85                  90                  95 cat gca gag aag aac tgg ttt gta ggc ctt aaa aaa aat ggt tcc tgt    457
His Ala Glu Lys Asn Trp Phe Val Gly Leu Lys Lys Asn Gly Ser Cys
            100                 105                 110 aag cgt gga cca cgg act cac tat ggc caa aag gct atc ttg ttc ctg    505
Lys Arg Gly Pro Arg Thr His Tyr Gly Gln Lys Ala Ile Leu Phe Leu
        115                 120                 125 cca cta cca gtg agc tcc gac taaggatccg aattcgagct ccgtcgacaa       556
Pro Leu Pro Val Ser Ser Asp
        130                 135 gcttgcggcc gcactcgagc accaccacca ccaccactga tccggctg ctaacaaagc    616 ccgaaaggaa gctg                                                    630

<210> SEQ ID NO 5
<211> LENGTH: 135
<212> TYPE: PRT
<213> ORGANISM: Homo sapiens

<400> SEQUENCE: 5

Met Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
```

```
                65                  70                  75                  80
Leu Glu Arg Leu Glu Glu Asn His Tyr Asn Thr Tyr Ile Ser Lys Lys
                    85                  90                  95
His Ala Glu Lys Asn Trp Phe Val Gly Leu Lys Lys Asn Gly Ser Cys
                100                 105                 110
Lys Arg Gly Pro Arg Thr His Tyr Gly Gln Lys Ala Ile Leu Phe Leu
        115                 120                 125
Pro Leu Pro Val Ser Ser Asp
    130                 135

<210> SEQ ID NO 6
<211> LENGTH: 630
<212> TYPE: DNA
<213> ORGANISM: Artificial Sequence
<220> FEATURE:
<223> OTHER INFORMATION: Chemically synthesized sequence for human
      acidic Fibroblast Growth Factor (140 amino acids) using preferred
      codons for E. coli
<221> NAME/KEY: CDS
<222> LOCATION: (122)...(544)

<400> SEQUENCE: 6
gcgtagagga tcgagatctc gatcccgcga aattaatacg actcactata ggggaattgt        60
gagcggataa caattcccct ctagaaataa ttttgtttaa ctttaagaag gagatataca       120 t atg ttt aac ctt ccg ccc ggg aat tac aaa aaa ccc aag ctt ctt tac       169
  Met Phe Asn Leu Pro Pro Gly Asn Tyr Lys Lys Pro Lys Leu Leu Tyr
   1               5                  10                  15 tgc agt aac gga gga cac ttc ctg cga att ctg cca gat ggc aca gta         217
Cys Ser Asn Gly Gly His Phe Leu Arg Ile Leu Pro Asp Gly Thr Val
                20                  25                  30 gat ggg act cgc gat cgc tcc gac cag cac att cag ctg caa ctc tcg         265
Asp Gly Thr Arg Asp Arg Ser Asp Gln His Ile Gln Leu Gln Leu Ser
            35                  40                  45 gcc gaa agc gtt gga gag gtc tat atc aag tcg acg gag act ggc cag         313
Ala Glu Ser Val Gly Glu Val Tyr Ile Lys Ser Thr Glu Thr Gly Gln
        50                  55                  60 tac ctt gcc atg gac acc gat ggg ctt ctg tat ggc tca cag acg cct         361
Tyr Leu Ala Met Asp Thr Asp Gly Leu Leu Tyr Gly Ser Gln Thr Pro
65                  70                  75                  80 aac gaa gaa tgc ttg ttt cta gaa aga cta gaa gaa aac cat tac aac         409
Asn Glu Glu Cys Leu Phe Leu Glu Arg Leu Glu Glu Asn His Tyr Asn
                85                  90                  95 acg tac ata tcg aaa aaa cat gca gag aag aac tgg ttt gta ggc ctt         457
Thr Tyr Ile Ser Lys Lys His Ala Glu Lys Asn Trp Phe Val Gly Leu
                100                 105                 110 aaa aaa aat ggt tcc tgt aag cgt gga cca cgg act cac tat ggc caa         505
Lys Lys Asn Gly Ser Cys Lys Arg Gly Pro Arg Thr His Tyr Gly Gln
        115                 120                 125 aag gct atc ttg ttc ctg cca cta cca gtg agc tcc gac taaggatccg          554
Lys Ala Ile Leu Phe Leu Pro Leu Pro Val Ser Ser Asp
    130                 135                 140 aattcgagct ccgtcgacaa gcttgcggcc gcactcgagc accaccacca ccaccactga       614
gatccggctg ctaaca                                                       630

<210> SEQ ID NO 7
<211> LENGTH: 141
<212> TYPE: PRT
<213> ORGANISM: Homo sapiens

<400> SEQUENCE: 7
```

```
Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
            35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
            115                 120                 125

Lys Ala Ile Leu Phe Leu Pro Leu Pro Val Ser Ser Asp
            130                 135                 140

<210> SEQ ID NO 8
<211> LENGTH: 154
<212> TYPE: PRT
<213> ORGANISM: Homo sapiens

<400> SEQUENCE: 8

Ala Glu Gly Glu Ile Thr Thr Phe Thr Ala Leu Thr Glu Lys Phe Asn
1               5                   10                  15

Leu Pro Pro Gly Asn Tyr Lys Lys Pro Lys Leu Leu Tyr Cys Ser Asn
            20                  25                  30

Gly Gly His Phe Leu Arg Ile Leu Pro Asp Gly Thr Val Asp Gly Thr
            35                  40                  45

Arg Asp Arg Ser Asp Gln His Ile Gln Leu Gln Leu Ser Ala Glu Ser
    50                  55                  60

Val Gly Glu Val Tyr Ile Lys Ser Thr Glu Thr Gly Gln Tyr Leu Ala
65                  70                  75                  80

Met Asp Thr Asp Gly Leu Leu Tyr Gly Ser Gln Thr Pro Asn Glu Glu
                85                  90                  95

Cys Leu Phe Leu Glu Arg Leu Glu Glu Asn His Tyr Asn Thr Tyr Ile
            100                 105                 110

Ser Lys Lys His Ala Glu Lys Asn Trp Phe Val Gly Leu Lys Lys Asn
            115                 120                 125

Gly Ser Cys Lys Arg Gly Pro Arg Thr His Tyr Gly Gln Lys Ala Ile
            130                 135                 140

Leu Phe Leu Pro Leu Pro Val Ser Ser Asp
145                 150
```

METHOD OF PRODUCING BIOLOGICALLY ACTIVE HUMAN ACIDIC FIBROBLAST GROWTH FACTOR AND ITS USE IN PROMOTING ANGIOGENESIS

RELATED APPLICATION

The present application claims priority to provisional patent application Ser. No. 60/225,406, entitled, "A Method of Producing Biologically Active Human Acidic Fibroblast Growth Factor and Its Use in Promoting Angiogenesis," filed on Aug. 15, 2000.

BACKGROUND OF THE INVENTION

1. Field of the Invention

The field of the invention relates to methods of producing a recombinant fibroblast growth factor protein and its use in promoting angiogenesis.

2. Description of the Related Art

Fibroblast growth factors (FGF) are nine structurally related polypeptides, which are potent regulators of cell proliferation, differentiation and normal development. They also take part in pathological processes of tumorogenesis and metastasis (Galzie, et al. Biochem. Cell Biol. (1997) 75: 669–685). They are potent mitogens and differentiation factors for a broad range of mesoderm and neuroectoderm derived cells, including endothelial cells.

The heparin proteoglycans, heparin or heparin sulfate, bind several FGF molecules together as a complex which are presented to the FGF receptors. FGF proteins bind to their receptors resulting in the activation of protein tyrosine kinases. The phosphorylation of these tyrosine kinases initiates multiple signals including the transcription of new mRNA's.

Two fibroblast growth factors, basic and acidic, are described as potent inducers of angiogenesis (Friesel et al. (1995) FASEB J. 9: 919–925). Both basic and acidic factors have been implicated in the control of blood vessel formation and their involvement in normal and pathological angiogenesis (Slavin, J. (1995) Cell Biology International 19(5): 431–444). These factors have been purified, their amino acid sequences have been determined and their cDNA has been cloned and sequenced.

Acidic Fibroblast Growth Factor (aFGF) has been described under various names including embryonic kidney-derived angiogenesis factor I, astroglial growth factor I, endothelial cell growth factor (ECGF), retina-derived growth factor, heparin-binding growth factor class 1, endothelial growth factor, eye-derived growth factor II, prostatropin, and glial maturation factor (Gospodarowicz, et al. (1987) Journal of Cellular Physiology supplement 5: 15–26). Cloning, nucleotide sequence and chromosome localization have been described (Jaye et al. (1986) Science 233: 541–545).

The aFGF gene is situated on chromosome 5. It has a single copy and encodes three exons separated by two introns. A 4.8 kb mRNA translates synthesis of a form of aFGF with 155 amino acids. However, the N-terminal methionine residue is removed in vivo to give a 154 amino acid form. This 154 amino acid form of the aFGF is processed into two forms which are 140 and 134 amino acids. The aFGF protein is an anionic mitogen of molecular weight 15,000–17,000 D.

The aFGF protein has been found in brain, retina, bone matrix and osteosarcoma. Only forms with 140 and 134 amino acids have been obtained from tissues. It has been suggested that the truncated aFGF forms are an artifact created by specific proteases during aFGF extraction and isolation (Gospodarowicz, et al. (1987) Journal of Cellular Physiology supplement 5: 15–26; Jaye et al. (1987) The Journal of Biological Chemistry 262 (34):16612–16617).

It has been suggested that heparin potentiates the biological activity of the aFGF protein (Thornton et al. (1983) Science 222 (4624): 623–625). Heparin binding to aFGF has been observed (Maciag et al. (1984) Science 225 (4665): 932–935). This heparin-binding characteristic has been used as an efficient affinity chromatography method for the purification of aFGF protein. Heparin potentiates the biological activity of aFGF and the enhanced activity of the aFGF-heparin complex varies from several to one hundred fold (Lobb, et al. (1986) Anal. Biochem. 154: 1–14).

SUMMARY OF THE INVENTION

In one embodiment, the present invention relates to a method for producing a biologically active human acidic fibroblast growth factor protein, including the steps of:

transforming a strain of E. coli with a plasmid having at least one copy of an expressible gene encoding a biologically active human acidic fibroblast growth factor protein, operably linked to a promoter;

infecting the transformed bacterial host cell with a bacteriophage λ capable of mediating delayed lysis; and cultivating the E. coli host cell under a culture condition that induces lytic growth of said cell without lysis until a desired level of production of said protein is reached, wherein said protein is produced as a soluble, biologically-active human acidic fibroblast growth factor protein.

In a preferred embodiment, the bacteriophage λ has a temperature-sensitive mutation. In a more preferred embodiment, the temperature-sensitive mutation is $cI_{857}$.

In a preferred embodiment, the E. coli host cells are grown at a temperature which prevents lytic growth of the bacteriophage λ prior to the cultivating step.

In a preferred embodiment, the bacteriophage λ has a mutation in at least one gene capable of mediating delayed lysis. In a more preferred embodiment the at least one gene capable of mediating delayed lysis is selected from the group consisting of N, Q and R.

In a preferred embodiment, the strain of E. coli produces a suppressor for the repair of amber-mutations.

In an alternate embodiment, the strain of E. coli lacks a suppressor for the repair of amber-mutations.

In a preferred embodiment, the infecting bacteriophage λ is provided at a multiplicity of infection in a range of about 1 to about 100. In a more preferred embodiment, the infecting bacteriophage λ is provided at a multiplicity of infection in a range of about 10 to about 25.

In a preferred embodiment, the bacteriophage-mediated delayed lysis of the strain of E. coli is delayed at higher multiplicities of infection relative to lower multiplicities of infection.

In a preferred embodiment, the biologically active human acidic fibroblast growth factor protein contains 154 amino acids. In a more preferred embodiment, the human acidic fibroblast growth factor protein has the sequence as set forth in SEQ ID NO: 8.

In a preferred embodiment, the promoter is a T7 polymerase promoter and the E. coli strain is capable of expressing the gene for T7 RNA polymerase. In a more preferred embodiment, the gene for T7 RNA polymerase gene is under the control of an inducible promoter. In an even more preferred embodiment, the inducible promoter is a lac UV 5 promoter.

In an alternate embodiment, the biologically active human acidic fibroblast growth factor protein contains 146 amino acids.

In another embodiment, the biologically active human acidic fibroblast growth factor protein contains 140 amino acids.

In another embodiment of the invention, the biologically active human acidic fibroblast growth factor protein contains 134 amino acids.

In a preferred embodiment, a method of producing a biologically active human acidic fibroblast growth factor protein is provided which comprises:

a) growing a first strain of *E. coli* cells, which harbor a strain of bacteriophage λ, wherein the bacteriophage λ has a temperature-sensitive mutation, b) adjusting the temperature to provide for lysis of the first strain of *E. coli* cells and release of the bacteriophage λ, c) providing a second strain of *E. coli* cells which have been transformed with a plasmid having at least one copy of an expressible gene encoding said biologically active human acidic fibroblast growth factor protein, said expressible gene being operably linked to a T7 polymerase promoter under the control of an inducible promoter, wherein the second strain of *E. coli* cells may be induced to express the gene for T7 RNA polymerase by addition of an inducer;

d) infecting the second strain of *E.coli* cells with the bacteriophage λ released from the first strain of *E. coli* cells; and e) incubating the infected second strain of *E. coli* cells in a culture medium containing the inducer, such that protein is produced and released into the culture medium upon lysis of the second strain of *E. coli* cells, wherein said protein is produced as a soluble, biologically-active protein at a concentration greater than 100 microgram/ml.

Another aspect of the invention encompasses a chemically synthesized nucleic acid having the sequence set forth in SEQ ID NO: 1.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1 shows the chemically synthesized nucleotide sequence for human acidic fibroblast growth factor (155 amino acids) (SEQ ID NO: 1) which has been modified by substitution of naturally occurring codons with codons found in highly expressed *E. Coli* proteins and the translated amino acid sequence (SEQ ID NO: 2).

FIG. 2 shows the modifications made in the chemically synthesized haFGF 155 codons. FGF fr HUMECGFB is the sequence obtained from GenBank (at NCBI) (SEQ ID NO: 3). HAFGF 155 is the chemically synthesized sequence of the present invention (SEQ ID NO: 1).

FIG. 6 shows the chemically synthesized nucleotide sequence for human acidic fibroblast growth factor (134 amino acids) (SEQ ID NO: 4) which has been modified by substitution of naturally occurring codons with codons found in highly expressed *E. coli* proteins and the translated amino acid sequence (SEQ ID NO: 5).

FIG. 8 shows the chemically synthesized nucleotide sequence for human acidic fibroblast growth factor (140 amino acids) (SEQ ID NO: 6) which has been modified by substitution of naturally occurring codons with codons found in highly expressed *E. coli* proteins and the translated amino acid sequence (SEQ ID NO: 7).

FIG. 11. Chicken embryo CAM blood vessels on the 14$^{th}$ day of development after FGF treatment. Formation of chicken egg CAM new blood vessels on the 4$^{th}$ day after application of the 154 amino acid form of the haFGF protein. Magnification 3x.

DETAILED DESCRIPTION OF THE PREFERRED EMBODIMENT

Figure 3:
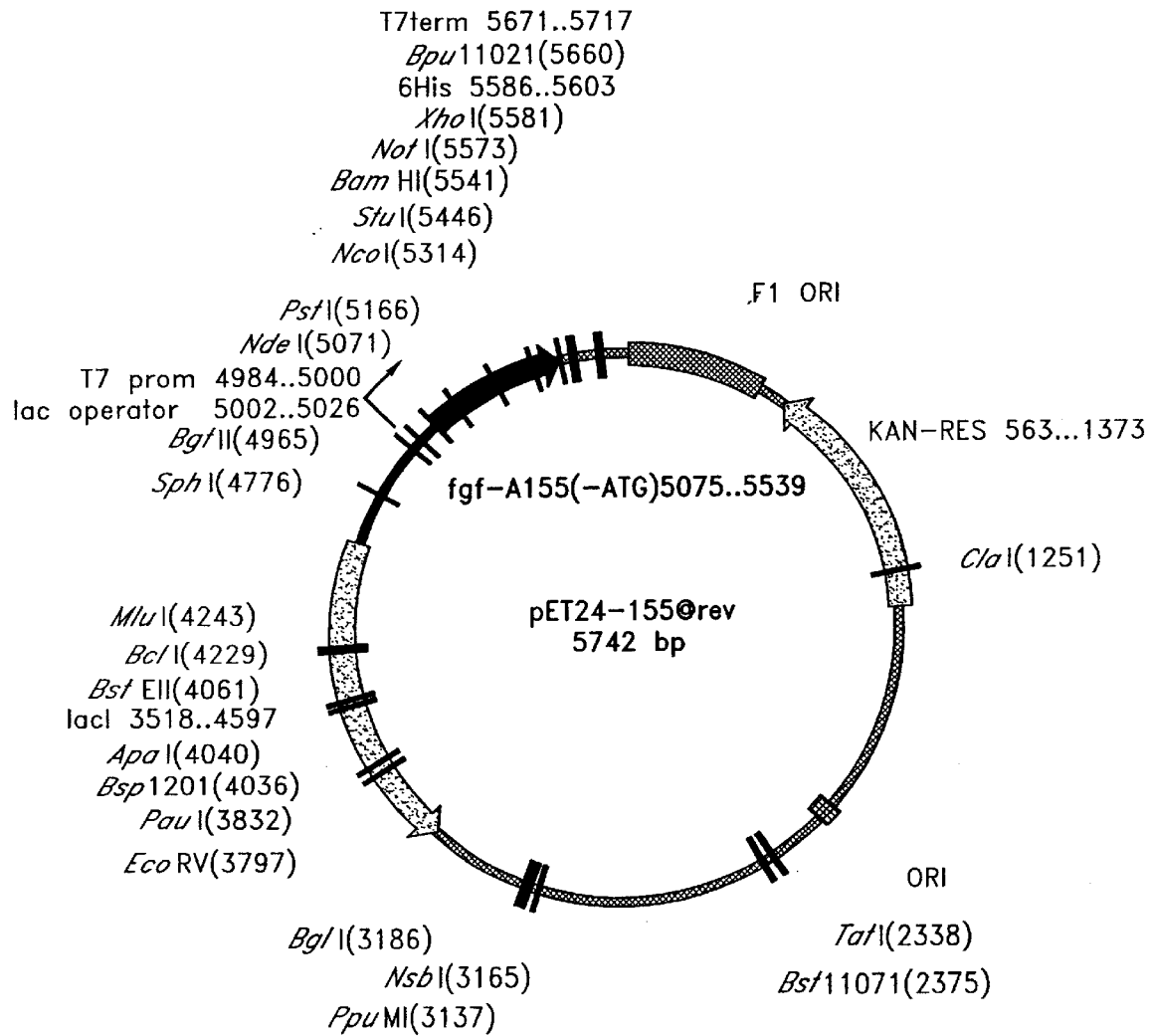
FIG. 3 shows the pET24-155@rev construct which contains the chemically synthesized haFGF 155 gene (SEQ ID NO: 1).

While the described embodiment represents the preferred embodiment of the present invention, it is to be understood that modifications will occur to those skilled in the art without departing from the spirit of the invention. The scope of the invention is therefore to be determined solely by the appended claims.

The haFGF155 gene encodes a protein containing 155 amino acid residues (SEQ ID NOS: 1 & 2). The first amino acid of the haFGF 155 sequence is the initiator methionine residue, which under normal situations would be removed during protein synthesis resulting in an FGF protein of 154 amino acids (SEQ ID NO: 8). However, it has only been possible to isolate two shorter aFGF forms from tissue samples. The two isolated forms contain 140 and 134 amino acid residues. The aFGF form containing 140 amino acids is considered complete, while the aFGF form containing 134 amino acids is considered to be truncated. It has not been possible to extract the aFGF form containing 155 or 154 amino acids from tissue samples. It is not known whether the shorter isoforms occur as a normal function of cell processing or as an artefact produced during the isolation procedure by specific proteases in the process of aFGF extraction. Western Blot analysis of the protein produced from the isolated DNA recombinant molecules for the three aFGF forms showed high expression of the 140 and 134 forms and a low expression level of the 154 form.

In a preferred embodiment of the present invention, the gene for human acidic fibroblast growth factor encodes the 154 amino acid form of the aFGF protein and is chemically synthesized (SEQ ID NO: 1). The nucleotide sequence of the haFGF 155 gene has been deduced on the basis of the previously described haFGF 155 amino acid sequence (SEQ ID NO: 2). The amino acid sequence of the synthesized haFGF155 gene does not differ from those previously described such as the translated sequence of the human aFGF nucleotide sequence of SEQ ID NO: 3 obtained from GenBank. However, the preferred nucleotide sequence of haFGF gene differs from those previously described. In a preferred embodiment of the present invention, the haFGF 155 gene has been chemically synthesized using the codons which are most often used by *E. coli* for intensively synthesized bacterial proteins. Preferred codon usage tables for *E coli* are well known and available. Chemical synthesis of polynucleotides was carried out using well known methodology (Edge et al. (1983) Nucleic Acids Research 11 (18): 6419–6435).

Alternatively, other well known forms of the haFGF gene could be used by those skilled in the art in the practice of the present invention including isolated DNA from animal tissues encoding other forms of the haFGF protein known to those skilled in the art including the 154, the 146, the 140 and 134 isoforms and any variants, derivatives, analogs or fragments thereof. The human aFGF proteins may be used in methods to stimulate angiogenesis. Human aFGF produced by the practice of the claimed invention may also be used in a composition with a suitable pharmaceutical carrier. Such carriers include, but are not limited to, saline, buffered saline, water, dextrose and combinations thereof. In a preferred embodiment, a fibringlue such as Tissucal™ (Baxter International, Duarte, Calif.) is used as carrier.

FIG. 1 shows the complete nucleotide sequence of the haFGF 155 gene, as synthesized by the present inventors (SEQ ID NO: 1). A sequence for human acidic fibroblast growth factor from GenBank (SEQ ID NO:3) was compared to the chemically synthesized sequence of FIG. 1. The comparison is shown in FIG. 2. There are distinctions in 80 codons.

Expression and cloning vectors typically contain a promoter that is recognized by the host organism and is operably linked to the haFGF nucleic acid. Promoters are untranslated sequences located upstream (5') to the start codon of a structural gene (generally within 100–1000 base pairs) that control the transcription and translation of particular nucleic acid sequences, such as the haFGF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by prokaryotic host cells are known. These promoters are operably linked to haFGF-encoding DNA by removing the promoter from the source DNA by restriction enzyme digestion and inserting the isolated promoter sequence into the vector.

Promoters known to those skilled in the art include β-lactamase and lactose promoter systems (Chang et al. (1978) Nature 275: 615; Goeddel et al. Nature (1979) 281: 544), alkaline phosphatase, and a tryptophan (trp) promoter system (Goeddel (1980) Nucleic Acids Research 8: 4057; Ep36,776). However, other known bacterial promoters are suitable. A most preferred promoter is the T7 promoter system. One skilled in the art would know how to ligate them to haFGF DNA using suitable linkers or adaptors to provide appropriate restriction sites. Promoters may also be used in tandem to achieve higher levels of expression.

Any number of prokaryote host cells are suitable for expressing the haFGF gene cloned into the vectors described herein. Preferred prokaryotic hosts include eubacteria such as Gram-negative or Gram-positive organisms, for example, Enterbacteriaceae such as Escherichia. A most preferred prokaryote host is *E. coli*.

Transformation means introducing DNA into an organism so that the DNA is capable of replication, either as an extrachromosomal element or by integration into the chromosome. Transformation of prokaryotic cells is performed using techniques well known to those skilled in the art such as treatment with $CaCl_2$ or electroporation.

An important advantage of infecting producer cells with a bacteriophage is that the phage causes a profound rearrangement of all macromolecular synthesis in the bacterial host cells. By turning off transcription of bacterial genes, phages may increase the copying of the targeted gene, and consequently, increase the output of desired product.

In one embodiment of the present super-production system, phage λ with amber-mutations that delay bacterial lysis (e.g., Q⁻ and R⁻ mutations) are provided in a strain of *E. coli*, designated Su°, which lacks the suppressor responsible for correcting amber-mutations in phage λ. In order to obtain a non-suppressing (Su°) strain of *E. coli*, Su° clones are selected from the wild-type Su⁺ population. Preferably, a selection marker is inserted into the phage DNA, e.g., tetracycline or ampicillin resistance.

Selection of non-suppressing (Su°) strains of *E. coli*, for example, *E. coli* K 802 was carried out with phage λ $cI_{857}N_{am7}N_{am53}$ bla tet (hereinafter λ bla N'). Strain *E. coli* C600 (λ bla N') served as source of the phage. This phage was obtained by insertion of plasmid pCV II (bla tet) at EcoRi site into single-site (EcoRI) vector carrying ts-mutation in repressor gene ($cI_{857}$). Then two amber-mutations were introduced into the phage N gene by recombination in vivo.

Clones were tested for non-lysogenicity with phage λ clear. In addition to phage λ bla N', phage λ $cI_{857}Q_{am117}R_{am54}$ was used to check for suppressor.

As is known, phage λ N' mutant is not able to lyse the host cells and is present in cells in the form of extremely unstable plasmids. If the host cells contain suppressor, the amber-mutation is phenotypically corrected, the N protein is synthesized and the phage can develop lytically. This difference in the viability of Su$^+$ and Su$^o$ cells, infected by λ N', is used as a basis for selection of spontaneously appearing Su$^o$ revertants from the E. coli Su$^+$ cell population. Phage λ with an inserted plasmid that introduced the ampicillin and tetracycline resistance markers into cells was used to prevent the nonlysing Su$^o$ cells from masking the search for mutants. The phage also contains ts-mutation in the repressor gene that permits lytic development of such phage resulting in cell lysis.

If the medium supplemented with ampicillin and tetracycline is inoculated with Su$^+$ culture after its infection with phage λ bla N' with subsequent growth at 43° C., single suppressor-free cells containing phage λ bla N' in the form of plasmids must develop on plates. Curing the cells from the phage, we must obtain Su$^o$ derivatives of the parent cultures. The method can be subdivided into several stages.

1. Infection of Culture With Phage λ bla N'

The culture E. coli Su was grown on the M9 medium with maltose at 37° C. under intense agitation to a density of 1–2×10$^8$ cells/ml. The cells were infected with phage λ bla N' at a multiplicity of 5–10 particles per cell and incubated for 20 min at 20° C. Under given conditions, the infection efficiency is about 100%, in addition to the bulk of Su+cells, the phage also infects single Su$^o$ cells.

2. Selection of Suppressor-Free Cells Containing Marker Phage

After infection, cells were plated out on agar medium supplemented with 12 γ/ml tetracycline and 20 γ/ml ampicillin and grown at 43° C. In 24 h, single colonies developed, which were replated on agar medium with antibiotics and grown at 37° C.

3. Curing of the Selected Clones From Phage λ bla N'

Since phage λ N' in the E. coli Su$^o$ cells is in the form of extremely unstable plasmids, in order to cure from the phage the selected clones were plated on selective agar medium without antibiotics and grown at 37° C. The number of cells that had lost the phage in the first passage on the medium without antibiotics amounted to 12–35%. The selection of such cells was carried out by monitoring the loss of antibiotic resistance and the acquisition of sensitivity to phage λ clear.

4. Testing of Cells for Repressor

The ability of phage λ with amber-mutations to form plaques on lawns of cured clones was checked. Isogenic suppressor-free derivatives of the parent E. coli Su$^+$ strains are clones, on which phage λ bla N' did not form plaques, phage λ cI$_{857}$Q$_{am117}$R$_{am54}$ produced 1–3×10$^5$ PFU/ml, and phage λ cI$_{857}$ without mutations in genes Q and R produced 1×10$^{10}$ PFU/ml.

Using this method, we obtained Su$^o$ revertants of E. coli K 802 Su$^+$. Based on the cell number at the moment of infection and the number of Su$^o$ revertants among them, the frequency of occurrence of suppressor-free cells was 3×10$^{-7}$.

In a preferred embodiment, the gene of interest is cloned into pET-24a(+) under the control of the T7 promoter. Preferred genes include, but are not limited to, genes encoding human aFGF 134 amino acid form, human aFGF 140 amino acid form, and human aFGF 146 amino acid form and human aFGF 155 amino acid form. In an alternate embodiment, the gene of interest may be cloned into both a bacterial plasmid and the λ phage under the control of appropriate promoters. In a most preferred embodiment, chemically synthesized haFGF 155 gene (SEQ ID NO: 1) is cloned into pET-24a(+) under the control of the T7 promoter.

The T7 promoter is recognized only by T7 RNA polymerase and is not recognized by the RNA polymerase of E. coli. The obtained plasmid with an haFGF gene was transformed into E. coli BL21(DE3). This strain contains the T7 RNA polymerase gene. The T7 RNA polymerase gene is under the control of the inducible lac UV5 promoter in order to induce T7 RNA polymerase synthesis only when necessary as this protein is toxic for the E. coli cell. The induction of the lac promoter is carried out by adding IPTG to the nutrient medium. In order to obtain a haFGF protein, the producer strain, containing the recombinant plasmid with the haFGF gene, is cultured under conditions of intensive aeration to a cell density of 5×10$^7$–5×10$^9$ cells in 1 ml at a temperature of 20–40° C. Then it is infected by lambda phage with the ts-mutation cI repressor gene with a multiplicity from 0.1 to 100 phage bodies per cell and incubation is continued at 20–37° C. for 2–14 hours. Simultaneously with the phage, IPTG at a concentration of 1 mM is introduced.

Production of the haFGF proteins was achieved by cultivation of the producer strain under conditions which slow down the lytic development of the lambda phage Such conditions include lowered temperature of cultivation and use of amber mutations in late lambda phage genes such as Q and R genes.

The haFGF proteins accumulated in the culture medium as a soluble proteins as a result of the producer strain cells lysis by lambda phage. The output of each haFGF protein generally constituted 20% of the soluble proteins accumulated in the culture medium. Debris was removed from the culture medium by centrifugation. The haFGF can then be purified from contaminant soluble proteins and polypeptides with the following procedures, which are exemplary of suitable purification procedures: by fractionation on an ion-exchange column; ethanol precipitation, reverse phase HPLC; chromatography on silica; immunoaffinity; SDS-PAGE; ammonium sulfate precipitation; and gel filtration. In one embodiment, the haFGF recombinant protein was purified using a C18 HPLC column. In another embodiment, the haFGF recombinant proteins were applied to heparin sepharose in order to obtain purified haFGF. The purified haFGF was then subjected to automated amino-terminal sequence analysis for 15 cycles. This analysis indicated that all the initiator methionine at position number 1 of FGF155 had been removed during synthesis resulting in the production of an FGF molecule containing 154 amino acids. The amino acids detected in cycles 2–14 of the above analysis were identical to positions 2–14 of FGF155.

Biological activity of the purified haFGF recombinant proteins was demonstrated by the ability to generate new vessels (angiogenesis). The assay involved the study of haFGF influence on the formation of new blood vessels using the model of chicken embryonic chorio-allantoic membrane (CAM).

A more detailed description of the present invention is provided below. While the described embodiment represents the preferred embodiment of the present invention, it is to be understood that modifications will occur to those skilled in the art without departing from the spirit of the invention. The scope of the invention is therefore to be determined solely by the appended claims.

EXAMPLE 1

Production of Human aFGF 154 by Phage-dependent Method

Cultures of *Escherichia coli* BL21(DE3) (NOVAGEN) were transformed by plasmid pET24-155 @rev (FIG. 3), which contains one copy of the chemically synthesized haFGF 155 gene encoding human acidic fibroblast growth factor (155 amino acids) (SEQ ID NO: 1). Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the chemically synthesized haFGF 155 gene (SEQ ID NO: 1) under the control of the T7 promoter to produce plasmid pET24-155 @rev. Expression of the haFGF 155 gene begins only after the appearance of T7 polymerase in the cells which is mediated through the induction of the lac UV5 promoter by IPTG.

Cultures of *E. coli* BL21(DE3) with pET24-155 @rev were grown with shaking at 37° C. in LB medium, containing 50 µg/ml kanamycin, to a density of $2\times10^8$ cells/ml. Then the cells were infected with phage $\lambda$ cI$_{857}$ Q$_{am117}$R$_{am54}$ at a multiplicity of about 10 phage bodies per 1 bacterial cell and cultivated with shaking at 21° C. for about 14 hour. Simultaneously with phage, 1 mM IPTG was introduced into the medium.

Phage $\lambda$ cI$_{857}$Q$_{am117}$R$_{am54}$ was prepared from lysogenic cultures of *E. coli* RLMI, which were grown in LB medium at 30° C. with intensive aeration to a density of approximately $1\times10^5$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1-2\times10^{10}$ PFU/ml.

After incubation with the phage-infected cells for 14 hours, debris was removed from the culture medium by centrifugation. The culture medium, containing the haFGF 154 protein was applied to a heparin sepharose column to obtain pure haFGF 154.

Figure 4:
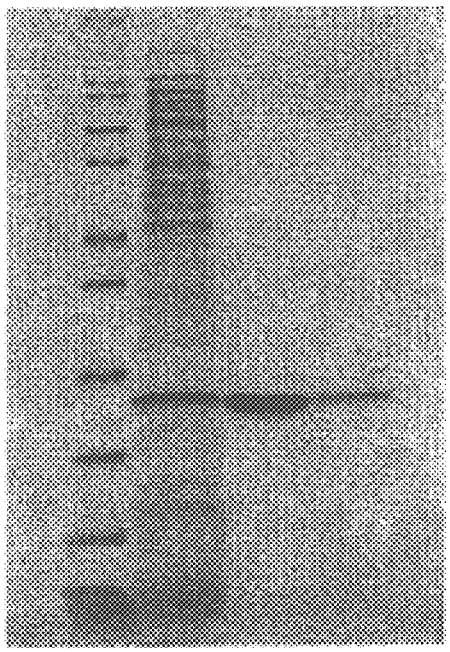
FIG. 4 shows purification of the culture medium containing recombinant baFGF 154 (SEQ ID NO: 8). In the electrophoregram: lane 1, crude media containing recombinant haFGF 154 (225 mg FGF-1/liter); lane 2, Heparin-Sepharose column purified recombinant haFGF 154; lane 3, purification of haFGF 154 by HPLC C-18 column. The unlabelled lane at the far left contains molecular weight markers.

The culture medium containing the haFGF 154 was analyzed by SDS-polyacrylamide gel electrophoresis under denaturing conditions and stained with Coomassie Blue. An electrophoregram of the culture medium, containing haFGF 154 protein is compared to purified haFGF protein in FIG. 4. Lane 1 shows crude media containing recombinant haFGF 154 (225 mg FGF-1/liter). Lane 2 shows Heparin-Sepharose column purified recombinant haFGF 154. Lane 3 shows purification of haFGF 154 by HPLC C-18 column. The unlabelled lane at the far left contains molecular weight markers. The overall purification yield was about 65%. Bioactivity was measured by two different assays, a 3T3 cell proliferation assay and a rat hind limb angiogenesis assay (not shown). The bioactivity was equipotent with FGF-1 obtained from Sigma-Chem. An assay using chicken embryo chorio-allantoic membrane is shown in Example 7, below.

The production of haFGF 154 protein in phage-infected cultures was about 20% of the total cellular protein. The molecular weight of haFGF 154 was 17,908 Daltons as determined by densitometer Image Master VDS (data not shown). N-terminal sequence analysis of FGF 154 indicated an alanine residue at the first position, with no initiator methionine detected.

EXAMPLE 2

Production of Human aFGF 134 Amino Acid Form by Phage-dependent Method

Figure 5:
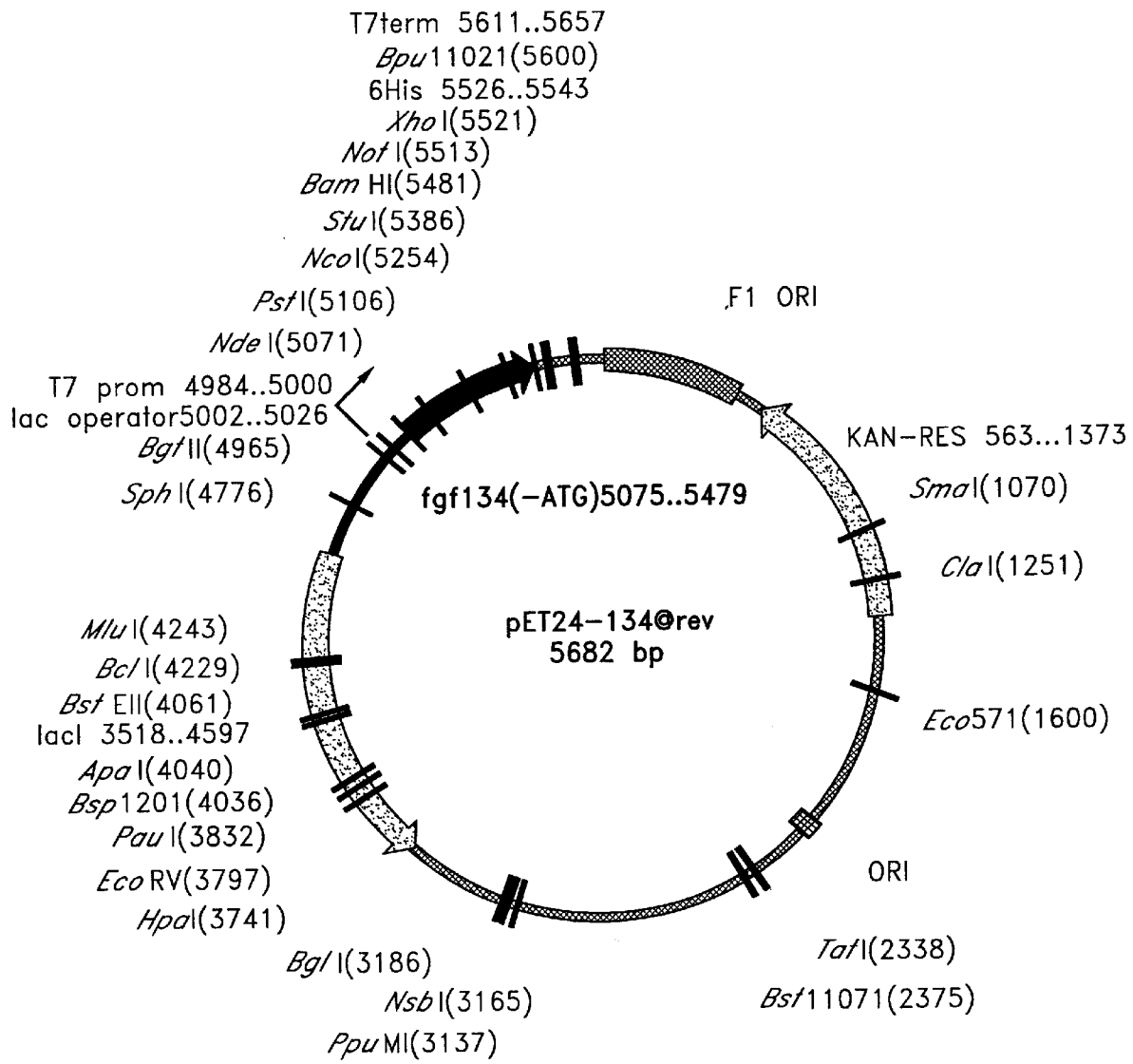
FIG. 5 shows the pET24-134@rev construct which contains the chemically synthesized haFGF 134 gene (SEQ ID NO: 4).

Cultures of *Eschericia coli* BL21(DE3) (NOVAGEN) were transformed by plasmid pET24-134 @rev (FIG. 5), which contains one copy of the chemically synthesized gene encoding human aFGF 134 amino acid form (FIG. 6; SEQ ID NO: 4). The translated amino acid sequence is shown in SEQ ID NO: 5. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 134 amino acid form gene under the control of the T7 promoter. Expression of the human aFGF 134 amino acid form gene begins only after the appearance of T7 polymerase in the cells which is mediated through the induction of the lac UV5 promoter by IPTG.

Cultures of *E. coli* BL21(DE3) with pET24-134 @rev were grown with shaking at 37° C. in LB medium, containing 50 µg/ml kanamycin, to a density of $2\times10^8$ cells/ml. Then the cells were infected with phage $\lambda$ cI$_{857}$Q$_{am117}$R$_{am54}$ at a multiplicity of about 10 phage bodies per 1 bacterial cell and cultivated with shaking at 21° C. for about 14 hour. Simultaneously with phage, 1 mM IPTG was introduced into the medium.

Phage $\lambda$ cI$_{857}$Q$_{am117}$R$_{am54}$ was prepared from lysogenic cultures of *E. coli* RLMI, which were grown in LB medium at 30° C. with intensive aeration to a density of approximately $1\times10^1$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1-2\times10^{10}$ PFU/ml.

After incubation with the phage-infected cells for 14 hours, debris was removed from the culture medium by centrifugation. The culture medium containing the haFGF 134 amino acid form was applied to a heparin sepharose column to obtain pure human aFGF 134 amino acid form.

EXAMPLE 3

Production of Human aFGF 140 Amino Acid Form by Phage-dependent Method

Figure 7:
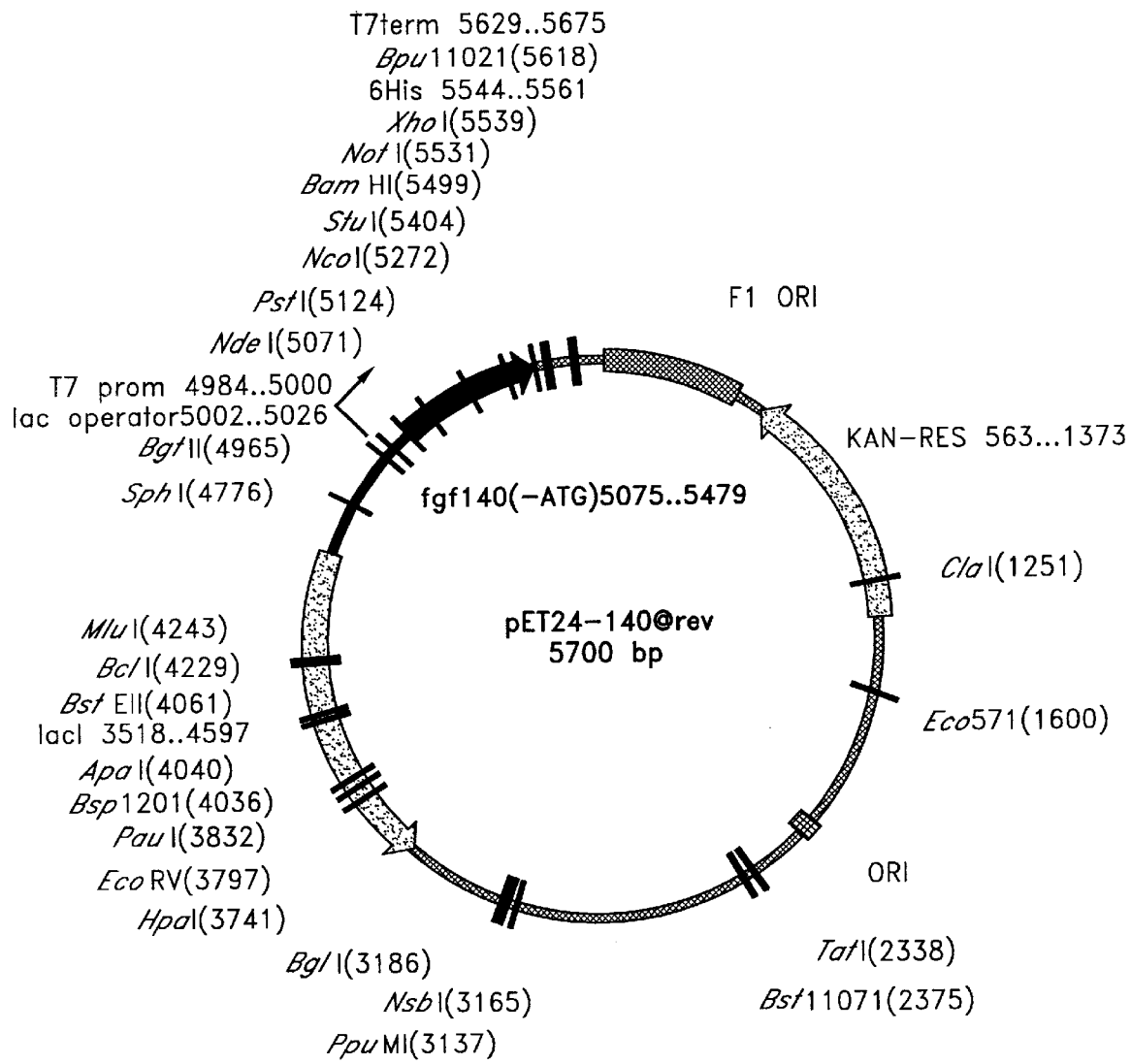
FIG. 7 shows the pET24-140@rev construct which contains the chemically synthesized haFGF 140 gene (SEQ ID NO: 6).

Cultures of *Eschericia coli* BL21(DE3) (NOVAGEN) were transformed by plasmid pET24-140 @rev (FIG. 7), which contains one copy of the chemically synthesized gene encoding human aFGF 140 amino acid form (FIG. 8; SEQ ID NO: 6). The corresponding protein is shown as SEQ ID NO: 7. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 140 amino acid form gene under the control of the T7 promoter. Expression of the human aFGF 140 amino acid form gene begins only after the appearance of T7 polymerase in the cells which is mediated through the induction of the lac UV5 promoter by IPTG.

Cultures of *E. coli* BL21(DE3) with pET24-140 @rev were grown with shaking at 37° C. in LB medium, containing 50 µg/ml kanamycin, to a density of $2\times10^8$ cells/ml.

Then the cells were infected with phage λ $cI_{857}Q_{am117}R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}Q_{am117}R_{am54}$ was prepared from lysogenic cultures of E. coli RLMI, which were grown in LB medium at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10$^{10}$ PFU/ml.

After incubation with the phage-infected cells for 14 hours, debris was removed from the culture medium by centrifugation. The culture medium containing the haFGF 140 amino acid form was applied to a heparin sepharose column to obtain pure human aFGF 140 amino acid form.

Human aFGF 140 produced by the method disclosed above had biological activity based upon the chick membrane assay (Example 6).

EXAMPLE 4

Production of Human aFGF 146 Amino Acid Form by Phage-dependent Method

Cultures of *Eschericia coli* BL21(DE3) (NOVAGEN) were transformed by plasmid pET24-146 @rev, which contains one copy of the chemically synthesized gene encoding human aFGF 146 amino acid form. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 146 amino acid form gene under the control of the T7 promoter. Expression of the human aFGF 146 amino acid form gene begins only after the appearance of T7 polymerase in the cells which is mediated through the induction of the lac UV5 promoter by IPTG.

Cultures of E. coli BL21(DE3) with pET24-146 @rev were grown with shaking at 37° C. in LB medium, containing 50 μg/ml kanamycin, to a density of 2×10$^8$ cells/ml. Then the cells were infected with phage λ $cI_{857}Q_{am117}R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}Q_{am117}R_{am54}$ was prepared from lysogenic cultures of E. coli RLMI, which were grown in LB medium at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10$^{10}$ PFU/ml.

After incubation with the phage-infected cells for 14 hours, debris was removed from the culture medium by centrifugation. The culture medium, containing the haFGF 146 amino acid protein, was applied to a heparin sepharose column to obtain pure human aFGF 146 amino acid form.

Human aFGF 146 produced by the method disclosed above had biological activity based upon the chick membrane assay (Example 6).

EXAMPLE 5

Purification of haFGF

The culture medium containing haFGF is diluted with one volume of 0.04M $KH_2PO_4$ buffer, pH 7.0, and applied to a heparin-sepharose column equilibrated with 0.02 M $KH_2PO_4$, pH 7.0. The flow rate is adjusted to 80 ml/hour. After application of the culture medium containing the haFGF protein, the column is washed with 0.02M $KH_2PO_4$ buffer, pH 7.0. Next, the column is washed with 0.02 M $KH_2PO_4$ buffer containing 0.6M NaCl, pH 7.3. Elution is carried out using 0.02 M $KH_2PO_4$ buffer with 1.5 M NaCl, pH 7.5. All steps are carried out at 4° C.

EXAMPLE 6

Gel Analysis of Recombinant Proteins Produced by the Pphage-dependent Method.

Figure 9:
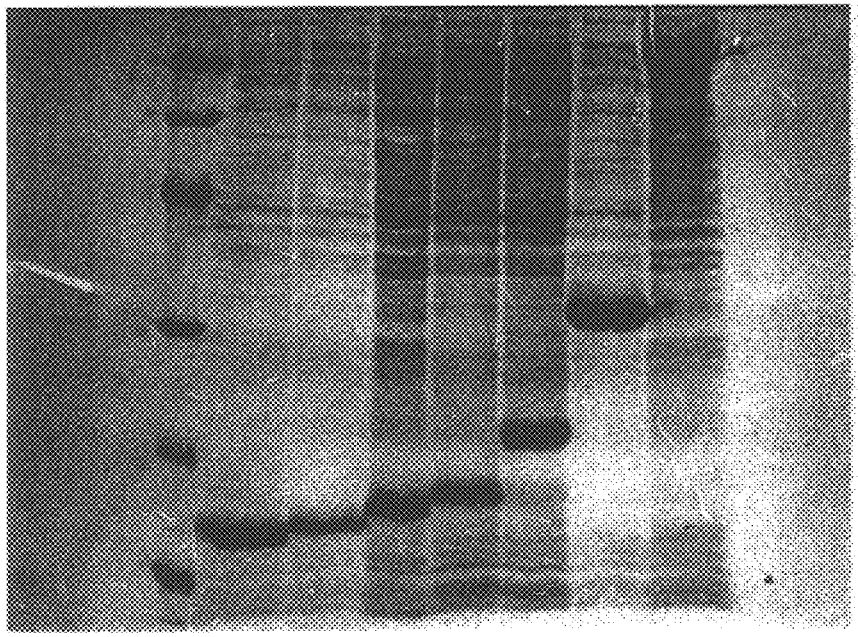
FIG. 9 shows a 12.5% SDS polyacrylamide gel containing proteins produced by the phage-dependent method described herein: lane 1: molecular weight standards, 2 μg each standard; lane 2: 40 μl of culture media containing the recombinant FGF 134 protein; lane 3: 40 μl of culture media containing the recombinant FGF 140 protein; lane 4: 40 μl of culture media containing recombinant interferon α2B; lane 5: 40 μl of culture media containing recombinant FGF 154 protein; lane 6: 40 μl of culture media containing recombinant human growth hormone; lane 7: 40 μl of culture media containing recombinant methionine aminopeptidase; lane 8: 40 μl of culture media containing β-galactosidase of *E. coli*.

Culture media containing human aFGF 134 amino acid form, human aFGF 140 amino acid form, and human aFGF 154 amino acid form were analyzed by SDS-polyacrylamide gel electrophoresis under denaturing conditions and stained with Coomassie Blue. An electrophoregram of culture media, containing human aFGF 134 amino acid form, human aFGF 140 amino acid form, human and aFGF 146 amino acid form was compared to molecular weight standards in FIG. 9. Lane 2 shows 30 μl of the culture medium containing human aFGF 134 amino acid form. Lane 3 shows 30 μl of culture media containing the recombinant FGF 140 protein. Lane 5 shows 30 μl of culture media containing recombinant FGF 154 protein. Lane 1 shows 2 μg of each molecular weight standard (Amersham Pharmacia Biotech). From the top, the molecular weight standards are: 94,000; 67,000; 43,000; 30,000; 20,100; and 14,400.

Quantitation of amounts of human aFGF 134 amino acid form, human aFGF 140 amino acid form, and human aFGF 154 amino acid form in a mixture was accomplished by scanning the stained protein bands on a polyacrylamide gel with densitometer Image Master VDS (Pharmacia Biotech). The production of the recombinant proteins in phage-infected cultures was about 20% of the total cellular protein.

Figure 10:
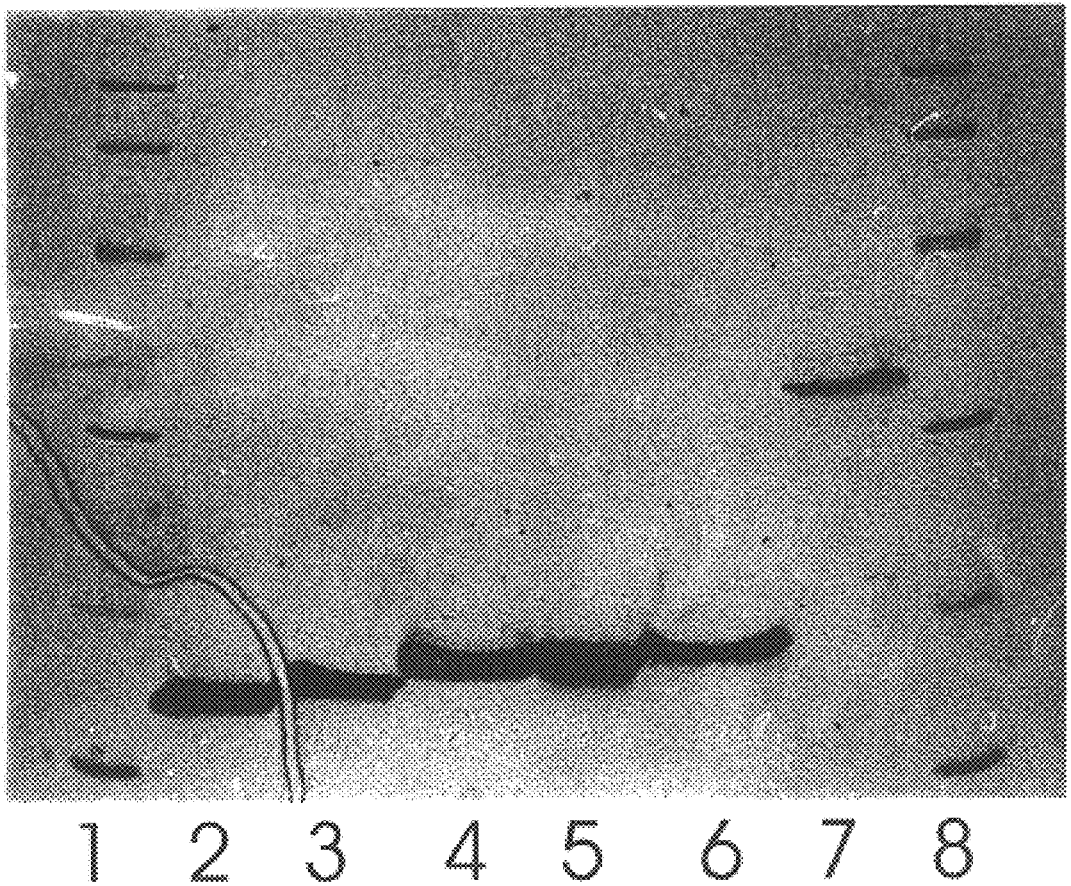
FIG. 10 shows a 12.5% SDS polyacrylamide gel containing recombinant proteins purified according to the presently claimed invention: lane 1: molecular weight standards; lane 2: 5 μg of purified FGF 134 protein; lane 3: 5 μg of purified FGF 140 protein; lane 4: 5 μg of purified FGF 146 protein; lane 5: 5 μg of purified interferon α2B protein; lane 6: 5 μg of purified FGF 154 protein; lane 7: 5 μg of purified methionine amino peptidase protein; and lane 8: molecular weight standards.

An electrophoregram containing purified recombinant human aFGF 134, haFGF 140, haFGF 146, and haFGF 154 protein was compared to molecular weight standards (FIG. 10). Lane 2 shows 5 μg of the purified aFGF 134 protein. Lane 3 shows 5 μg of the purified human aFGF 140. Lane 4 shows 5 μg of the purified human aFGF 146 amino acid form. The production of human aFGF 146 amino acid form in phage-infected cultures was about 20% of the total cellular protein. Lane 6 shows 5 μg of haFGF 154 protein. Lanes 1 and 8 show 2 μg of each molecular weight standard (Amersham Pharmacia Biotech).

EXAMPLE 7

A Method of Studying FGF Influence on the Formation of New Blood Vessels in the Chicken Embryo Chorio-allantoic Membrane (CAM).

The method of studying angiogenesis on the model of chicken embryos (Thomas et al. (1985) Proc. Natl. Acad. Sci, USA 82: 6409–6413) was adapted to determine the effects of the haFGF 154, 146, and 140 recombinant proteins on angiogenesis compared to pure brain-derived acidic fibroblast growth factor. Pure brain-derived acidic fibroblast growth factor is a potent angiogenic vascular endothelial cell mitogen with sequence homology to interleukin.

The shells of three-day old chicken embryos were sterilized with ethyl alcohol. The shell and under shell cover were removed from the air chamber using forceps and the eggs were covered by the bottom of a plastic 35 mm Petri dish. The embryos were incubated at 37° C. for 5–6 days. At the end of this period, the embryos were examined and the eggs with well-developed blood vessels of CAM were selected for experimentation.

Filter paper disks with deposited gel containing FGF were laid on the eggs CAM with the gel towards the blood vessels and incubated in a thermostat at 37° C. for another 3 days. The gel was prepared in the following way: the tested quantity of FGF was dissolved in 30 μl of Eagle's medium (solution 1); then in 30 μl of Eagle's medium, 10 μg of heparin was dissolved and 2% of agarose added (solution 2). Then equal volumes of solution 1 and 2 were mixed and the obtained mixture was deposited in aliquots by 60 μl on 12 mm diameter filter paper disks.

On the 4th day, the filter paper disks were removed. Rich cow milk (10% milkfat) was injected under CAM in a quantity of about 1 ml or less. The result was a white background against which the CAM vessels were easily observed.

The results of the experiment were recorded with a video camera in conjunction with a computer. The formation of new CAM vessel under the affect of FGF was evaluated by the following parameters: the nature and direction of vessel growth, their quantity and quality (large, medium, small), the presence or absence of anastomosis, etc. These data were compared with the control samples which had not been exposed to FGF. FIG. 11 shows Chicken embryo blood vessels on the 14th day of development after treatment with FGF154 produced by the phage-dependent recombinant method described herein and purified on heparin sepharose as described.

Figure 11A:
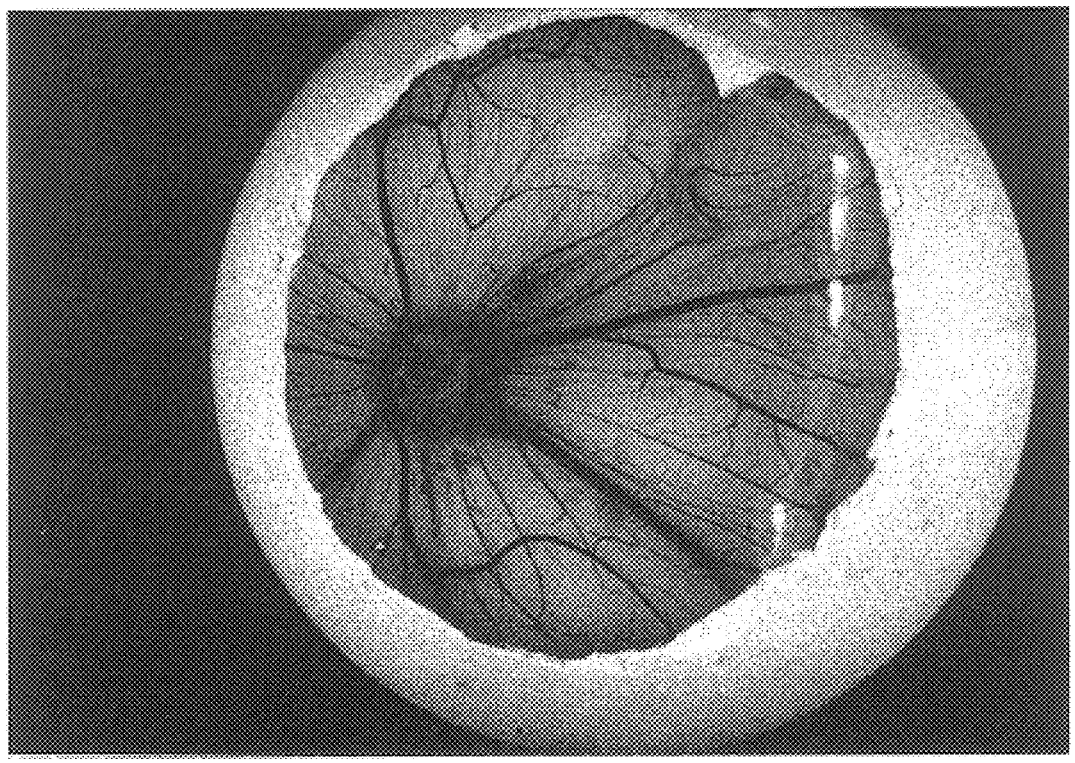
FIG. 11A shows the effect of 1 μgm of the 154 amino acid form of the haFGF protein. The vessels under application are mainly small and show radial growth.
Figure 11B:
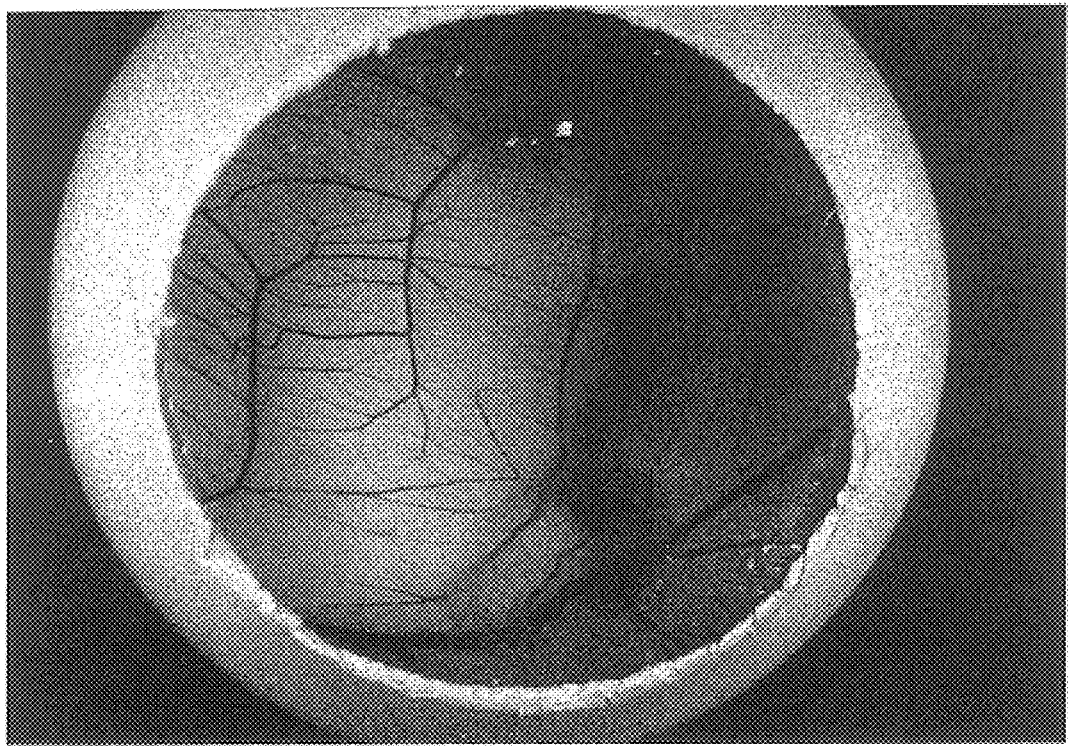
FIG. 11B shows the control sample.

FIG. 11A demonstrates the correlation between application of recombinant FGF154 protein and the formation of new blood vessels. On the fourth day after application of 1 μg of FGF154, vessels are mainly small and show radial growth (FIG. 11A). Increasing the amount of FGF154 to 3 μg results in a corresponding increase in the size of the blood vessels (not shown). Medium vessels are observed with radial growth. A further increase to 4 μg of FGF154 applied (not shown) results in development of large, medium and small blood vessels at 4 days after application. Untreated control is shown in FIG. 11B.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for producing a biologically active human acidic fibroblast growth factor protein, comprising:

transforming an *E. coli* host cell with a plasmid comprising an expressible gene encoding a biologically active human acidic fibroblast growth factor protein, having a sequence selected from the group consisting of SEQ ID NO: 2, amino acids 9–155 as shown in SEQ ID NO: 2, SEQ ID NO: 5. SEQ ID NO: 7, and SEQ ID NO: 8, operably linked to a promoter;

infecting the transformed bacterial host cell with a bacteriophage λ, which mediates delayed lysis; and cultivating the *E. coli* host cell under a culture condition that induces lytic growth of said cell without lysis until a desired level of production of said protein is reached, wherein said protein is produced as a soluble, biologically-active human acidic fibroblast growth factor protein.

2. The method of claim 1, wherein the bacteriophage λ has a temperature-sensitive mutation which is $cI_{857}$.

3. The method of claim 1, wherein prior to the cultivating step, the *E. coli* host cells are grown at a temperature between 20–37° C. which prevents lytic growth of the bacteriophage λ.

4. The method of claim 1, wherein the bacteriophage λ has a mutation in at least one gene which mediates delayed lysis.

5. The method of claim 4, wherein the at least one gene which mediates delayed lysis is selected from the group consisting of N, Q and R.

6. The method of claim 1, wherein the *E. coli* host cell produces a suppressor for the repair of amber-mutations.

7. The method of claim 1, wherein the *E. coli* host cell lacks a suppressor for the repair of amber-mutations.

8. The method of claim 1, wherein the infecting bacteriophage λ is provided at a multiplicity of infection in a range of about 1 to about 100.

9. The method of claim 1, wherein the infecting bacteriophage λ is provided at a multiplicity of infection in a range of about 10 to about 25.

10. The method of claim 1, wherein bacteriophage-mediated delayed lysis of the *E. coli* host cell is delayed at higher multiplicities of infection relative to lower multiplicities of infection.

11. The method of claim 1, wherein the human acidic fibroblast growth factor protein has the sequence as set forth in SEQ ID NO: 8.

12. The method of claim 1, wherein the promoter is a T7 polymerase promoter and the *E. coli* host cell comprises a gene for T7 RNA polymerase.

13. The method of claim 12, wherein the gene for T7 RNA polymerase gene is under the control of an inducible promoter.

14. The method of claim 13, wherein the inducible promoter is a lac UV 5 promoter.

15. The method of claim 1, wherein the biologically active human acidic fibroblast growth factor protein contains amino acids 9–155 as shown in SEQ ID NO: 2.

16. The method of claim 1, wherein the biologically active human acidic fibroblast growth factor protein has the sequence set forth in SEQ ID NO: 7.

17. The method of claim 1, wherein the biologically active human acidic fibroblast growth factor protein has the sequence set forth in SEQ ID NO:5.

18. The method of claim 1, wherein the DNA encoding the expressible gene comprises the polynucleotide of SEQ ID NO: 1.

* * * * *